(12) United States Patent
Vachon et al.

(10) Patent No.: US 12,269,905 B2
(45) Date of Patent: Apr. 8, 2025

(54) COPOLYMER OF ETHYLENE AND ION PAIR COMPOUND

(71) Applicant: SABIC GLOBAL TECHNOLOGIES B.V., Bergen Op Zoom (NL)

(72) Inventors: Jerome Vachon, Geleen (NL); Peter Neuteboom, Geleen (NL); Jonathan Tellers, Geleen (NL)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 596 days.

(21) Appl. No.: 17/627,433

(22) PCT Filed: Jul. 16, 2020

(86) PCT No.: PCT/EP2020/070097
§ 371 (c)(1),
(2) Date: Jan. 14, 2022

(87) PCT Pub. No.: WO2021/009274
PCT Pub. Date: Jan. 21, 2021

(65) Prior Publication Data
US 2022/0259340 A1     Aug. 18, 2022

(30) Foreign Application Priority Data
Jul. 18, 2019   (EP) .................................... 19187151

(51) Int. Cl.
*C08F 210/02*     (2006.01)
*C07C 57/04*      (2006.01)

(52) U.S. Cl.
CPC ............ *C08F 210/02* (2013.01); *C07C 57/04* (2013.01)

(58) Field of Classification Search
USPC ................................ 526/277, 287, 307, 923
See application file for complete search history.

(56) References Cited

U.S. PATENT DOCUMENTS

| | | | |
|---|---|---|---|
| 3,264,272 A | 8/1966 | Rees et al. | |
| 3,308,081 A * | 3/1967 | Glabisch | C08F 210/02 526/263 |
| 3,928,269 A * | 12/1975 | Taylor | C08K 5/3475 526/923 |
| 5,250,642 A | 10/1993 | Ahmed et al. | |
| 5,270,415 A | 12/1993 | Sulc et al. | |

FOREIGN PATENT DOCUMENTS

| | | | |
|---|---|---|---|
| EP | 0487975 A1 | 6/1992 | |
| WO | 9847937 A | 10/1998 | |
| WO | WO2018/094018 A1 * | 5/2018 | C08L 23/08 |

OTHER PUBLICATIONS

Salamone, et al. "Acrylic ampholytic inomers", Polymer, 1982, vol. 23, June, p. 843-848.

Vanhoorne et al., "Low-Shear Melt Rheology of Partially-Neutralized Ethylene-Methacrylic Acid Ionomers", Macromolecules 29 (1996) 598-604.

(Continued)

*Primary Examiner* — Fred M Teskin
(74) *Attorney, Agent, or Firm* — CANTOR COLBURN LLP

(57) ABSTRACT

The invention relates to an ethylene copolymer obtained by copolymerizing ethylene and an ion pair compound consisting of a cation of formula (I) and an anion selected from formulas (II), (III), (IV) and (V), wherein (I) where R1=H or C1-C10 alkyl; X=O or NH; R2=C1-C40 alkyl; R3, R4=H or C1-C10 alkyl which can be connected through a cyclic structure, R5=H or C1-C20, (II) (III) (IV) (V) where R6, R7, R9=H or C1-C10 alkyl; R8, R10=C1-C40 alkyl; Y, V, W=O or NH; n=1 to 20; Z=—SO³ or —C(O)O.

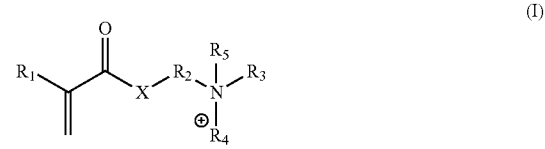

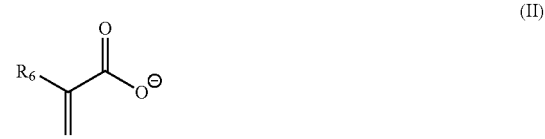

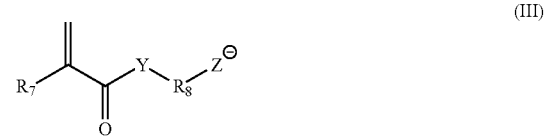

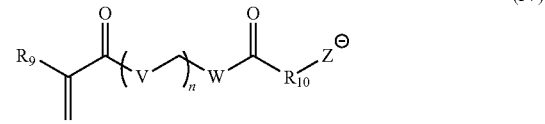

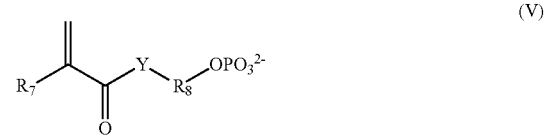

18 Claims, 2 Drawing Sheets

(56) References Cited

OTHER PUBLICATIONS

Grady et al., "X-ray absorption spectroscopy studies of zinc-neutralized ethylene-methacrylic acid ionomers", Polymer, 40, (1999) 283-288.
International Search Report for International Application No. PCT/EP2020/070097, International Filing Date Jul. 16, 2020, Date of Mailing Oct. 14, 2020, 5 pages.
Written Opinion for International Application No. PCT/EP2020/070097, International Filing Date Jul. 16, 2020, Date of Mailing Oct. 14, 2020, 8 pages.

* cited by examiner

COPOLYMER OF ETHYLENE AND ION PAIR COMPOUND

CROSS REFERENCE TO RELATED APPLICATIONS

This application is a National Stage application of PCT/EP2020/070097, filed Jul. 16, 2020, which claims the benefit of European Application No. 19187151.6, filed Jul. 18, 2019, both of which are incorporated by reference in their entirety herein.

BACKGROUND

The present invention relates to an ion pair compound. The invention further relates to an ethylene copolymer of ethylene and an ion pair compound and its applications.

Ionomers are well known material having specific physical properties in terms of electrical conductivity and viscosity, and is described e.g. in U.S. Pat. No. 3,264,272. The most commonly used ionomer is commercialized by Dupont under the name Surlyn®. The production of Surlyn® involves the copolymerization of ethylene and methacrylic acid via a high-pressure free radical reaction which results in an acidic copolymer. Once the copolymer is synthesized, a second step called neutralization step is needed involving the use of metal cations such as zinc, sodium, and magnesium to neutralize the acidic copolymer. The neutralization step typically mixes the copolymer in the melt with a basic metal hydroxide such as zinc oxide or zinc acetate (see B. P. Grady et al., Polymer 40 (1999) 283-288). Neutralization can also be achieved through solution processes, in which case the copolymer is dissolved using a toluene/alcohol (e.g n-butanol) mix and partially neutralized using sodium, magnesium or zinc salts in solution (e.g 0.5 M NaOH is added). The solvent is then removed leaving the neutralized copolymer (ionomer) as the final product (see P. Vanhoorne et al., Macromolecules 29 (1996) 598-604)). This ionomer is used as a coating and packaging material.

Ionomers may be zwitterionic. Zwitterionic ionomers bear in the same polymer chain both positive and negative charges (without the presence of counter ions such as sodium for purely anionic ionomers). This provides a dynamic bonding feature leading to a structurally dynamic polymer architecture. This type of material is known to be responsive to external stimuli (such as temperature or pH) but also can be used as self-healing and shape memory polymers. Moreover, enhanced mechanical properties can be expected due to energy dissipative bond re-arrangement. Typical examples are making use of hydrogen bonding "Supramolecular" polymers which are able to act as dynamic crosslinks giving rise to complex viscoelastic behavior.

The production of Surlyn® requires corrosion resistant equipment due to the use of pure methacrylic acid, which is rather toxic and corrosive. In case the neutralization step is performed in solution, solvents are required which need to be evaporated from the material which increases energy consumption and waste. In case the neutralization step is performed in the melt, unreacted neutralizing salt might remain in the commercial ionomer since the industrial process relies on mechanical mixing to overcome possible cation transport limitations, as explained in B. P. Grady et al., Polymer 40 (1999) 283-288). In commercial Surlyn®, the neutralization is only partial and acid groups are still present within the polymer backbone. This is disadvantageous because Surlyn® materials need to be dried thoroughly before extruding, since they inherently absorb moisture. The hygroscopic nature of Surlyn® can potentially leads to the corrosion of extruder screws and barrels. It is being noted that the plastic blown film manufacturers tend to prefer polyethylene made with Metallocene catalysts (over Surlyn®), as the latter ones do not involve drying, do not lead to corrosion of processing equipments, apart from being lower cost compared to Surlyn®.

WO98/47937, U.S. Pat. Nos. 5,270,415 and 5,250,642 disclose several types of ion pair compounds. WO98/47937, U.S. Pat. Nos. 5,270,415 and 5,250,642 do not disclose an ethylene copolymer.

There is a need for a material which allows production of an ionomer wherein the above-mentioned and/or other problems are solved.

SUMMARY

Accordingly, the invention provides an ion pair compound consisting of
a cation of formula (I) and an anion selected from formulas (II), (III), (IV), (V) and (VI), wherein where R1=H or C1-C10 alkyl; X=O or NH; R2=C1-C40 alkyl; R3, R4=H or C1-C10 alkyl which can be connected through a cyclic structure; R5=H or C1-C20, where R6, R7, R9=H or C1-C10 alkyl; R8, R10=C1-C40 alkyl; Y, V, W=O or NH; n=1 to 20; Z=—SO$^3$ or —C(O)O.

The molar ratio of the cation (I) and the anion (II), (III) or (IV) in the ion pair compound is 1:1. The molar ratio of the cation (I) and the anion (V) or (VI) in the ion pair compound is 2:1.

DETAILED DESCRIPTION

It is noted that the following ion pair compound disclosed in POLYMER, 1982, Vol 23, June, p. 843 is excluded from the ion pair compound of the present invention:

It is further noted that the following ion pair compounds disclosed in EP487975 are excluded from the ion pair compound of the present invention:

An ion pair compound wherein the cation is 2-methacryloyloxyethyltrimethylammonium and the anion is 2-acrylamido-2-methylpropane sulfonate or 2-methacryloyloxyethane sulfonate.

The invention further provides an ethylene copolymer obtained by copolymerizing ethylene and an ion pair compound consisting of a cation of formula (I) and an anion selected from formulas (II), (III), (IV), (V) and (VI).

Unlike methacrylic acid, using the ion pair compound for the production of the ethylene copolymer according to the invention does not require a corrosion resistant equipment.

The ethylene copolymer of the invention is a zwitterionic ionomer. The copolymerization uses an ion pair compound according to the invention, where the acid (precursor of the anion) is fully neutralized by a base (precursor of the cation), and thus the obtained ethylene copolymer does not comprise a free acid. Hence, it is an advantage of the process of the invention that no neutralization step is required after the copolymerization.

Preparation of the Ion Pair Compound

The ion pair compound according to the invention may be prepared in the following ways depending on whether each of the precursor of anion and cation is present as a base salt/acid salt or a free base/acid.

a) Preparation from Base Salt and Acid Salt

In some cases, the ion pair compound according to the invention is prepared by mixing a base salt (IA) and an acid salt (IIA) to (VIA) in a polar, organic solvent.

(IA)

wherein A is a halogen

(IIA)

(IIIA)

(IVA)

(VA)

(VIA)

wherein B+ in formulas (IIA), (IIIA) and (IVA) represents an alkali metal ion and B2+ in formulas (VA) and (VIA) represents two alkali metal ions or an alkaline earth metal ion.

R1-R10, X, Y, Z, V, W and n in (IA)-(VIA) represent groups as mentioned for R1-R10, X, Y, Z, V, W and n in (I)—(VI).

In this case, mixing the compound (IA) with a compound selected from (IIA) to (VIA) results in a composition comprising the ion pair compound according to the invention and an inorganic salt by ion-exchange metathesis. The ion pair compound according to the invention is organic and can be separated from the inorganic salt by the solubility difference of the organic salt versus the inorganic salt.

Depending on solubilities of the starting base salt (IA) and acid salt (IIA to VIA), following approaches can be envisioned to perform such ion-exchange metathesis:

If both base salt and acid salt are not soluble in water but soluble in polar organic solvents (e.g. ethanol, DCM), the acid salt and the base salt react in an organic solvent. The organic ion pair compound according to the invention and an inorganic salt are formed. The organic ion pair compound according to the invention remains in the organic solvent and the inorganic salt will precipitate from the organic solvent. The ion pair compound can be isolated by filtering out the precipitated inorganic salt and evaporating the organic solvent.

If either the base salt or the acid salt is soluble in water and the other is not soluble in water but soluble in polar organic solvents not miscible with water (e.g. DCM), stirring the mixture of the base salt in water and acid salt in organic solvent or of the base salt in organic solvent and acid salt in water results in the formation of the organic ion pair compound according to the invention and an inorganic salt. Subsequently, a biphasic mixture will be formed consisting of an organic phase comprising the ion pair compound and a water phase comprising the inorganic salt. The ion pair compound can be isolated by removing the water phase and evaporating the organic solvent.

b1) Preparation from Base Salt and Free Acid

In some cases, the ion pair compound according to the invention is prepared by mixing a base salt (IA) and a free acid selected from (IIB) to (VIB) in a polar, organic solvent in the presence of an inorganic base.

R6-R10, Y, Z, V, W and n in (IIB)—(VIB) represent groups as mentioned for R6-R10 in (II)—(VI).

In this case, mixing the base salt (IA) with a free acid selected from (IIB) to (VIB) results in a composition comprising the ion pair compound according to the invention and an inorganic salt made from the base salt and the inorganic base (ion-exchange metathesis). The ion pair compound according to the invention is organic and can be separated from the inorganic salt by the solubility difference of the organic salt versus the inorganic salt in a similar manner as explained for method a).

Examples of suitable inorganic base includes NaOH and KOH.

b2) Preparation from Free Base and Acid Salt

In some cases, the ion pair compound according to the invention is prepared by mixing a free base (IB) and an acid salt selected from (IIA) to (VIA) in a polar, organic solvent in the presence of an inorganic acid.

R1-R4 and X and n in (IB) represent groups as mentioned for R1-R4 and X in (I).

In this case, mixing the free base (IB) with an acid salt selected from (IIA) to (VIA) results in a composition comprising the ion pair compound according to the invention and an inorganic salt made from the acid salt and the inorganic acid. In the resulting ion pair compound, R5 is H. The ion pair compound according to the invention is organic and can be separated from the inorganic salt by the solubility difference of the organic salt versus the inorganic salt in a similar manner as explained for method a).

Examples of suitable inorganic acid includes HCl and $H_2SO_4$.

c) Preparation from Free Base and Free Acid

In some cases, the ion pair compound according to the invention is prepared by mixing a free base (IB) and a free acid selected from (IIB) to (VIB). In this case, mixing the free base (IB) with a free acid selected from (IIB) to (VIB) results in the ion pair compound according to the invention. In the resulting ion pair compound, R5 is H.

If at least one of the free base and the free acid can be brought to a liquid state, the preparation is advantageously performed without the use of a solvent. The mixing of the free base and the free acid may be done by a dropwise addition of the free base or the free acid in a liquid state to the other component, possibly while controlling the temperature (with e.g. an ice bath). This is particularly preferred since no separation is necessary after the formation of the ion pair compound.

If neither of the free base and the free acid cannot be brought to a liquid state, the reaction is performed in the presence of an organic solvent. The ion pair compound can be isolated by evaporating the organic solvent.

Preferred Formulas of Cation (I), Base Salt (IA), Free Base (IB)

Preferably, R1=H or CH3.
Preferably, X=O.
Preferably, R2=$CH_2$—$CH_2$.
Preferably, R3=R4=R5=H; R3=R4=CH3, R5=H; R3=R4=Et, R5=H; R3=tButyl, R4=R5=H or R3=R4=R5=CH3.

Examples of particularly preferred embodiments include the following:
(I), (IA), (IB) wherein R1=H, X=O, R2=$CH_2$—$CH_2$, R3=R4=R5=H
(I), (IA), (IB) wherein R1=H, X=O, R2=$CH_2$—$CH_2$, R3=R4=Me, R5=H
(I), (IA), (IB) wherein R1=H, X=O, R2=$CH_2$—$CH_2$, R3=R4=Et, R5=H
(I), (IA), (IB) wherein R1=H, X=O, R2=$CH_2$—$CH_2$, R3=tButyl, R4=R5=H
(I), (IA), (IB) wherein R1=H, X=O, R2=$CH_2$—$CH_2$, R3=R4=R5=CH3
(I), (IA), (IB) wherein R1=CH3, X=O, R2=$CH_2$—$CH_2$, R3=R4=R5=H
(I), (IA), (IB) wherein R1=CH3, X=O, R2=$CH_2$—$CH_2$, R3=R4=CH3, R5=H
(I), (IA), (IB) wherein R1=CH3, X=O, R2=$CH_2$—$CH_2$, R3=R4=Et, R5=H
(I), (IA), (IB) wherein R1=CH3, X=O, R2=$CH_2$—$CH_2$, R3=tButyl, R4=R5=H
(I), (IA), (IB) wherein R1=CH3, X=O or NH, R2=$CH_2$—$CH_2$, R3=R4=R5=Me Preferably, the free base (IB) is selected from the group consisting of:
2-(Dimethylamino)ethyl acrylate
2-(Diethylamino)ethyl acrylate 2-(Diethylamino)ethyl methacrylate
2-(Dimethylamino)ethyl methacrylate
2-(tert-Butylamino)ethyl methacrylate
N-[3-(hexahydro-1H-azepin-1-yl)-1,1-dimethylpropyl]-2-Propenamide
N-[2-(tetrahydro-1,4-oxazepin-4(5H)-yl)ethyl]-2-Propenamide
N-[2-[methyl(tetrahydro-2H-pyran-4-yl)amino]ethyl]-2-Propenamide
N-[3-(hexahydro-4-methyl-1H-1,4-diazepin-1-yl)propyl]-2-Propenamide
N-[1-methyl-2-(methylamino)propyl]-2-Propenamide,
N-[2-(methylamino)propyl]-2-Propenamide,
N-[2-methyl-2-(methylamino)propyl]-2-Propenamide
N-[1-methyl-2-(methylamino)ethyl]-2-Propenamide
N-[1-methyl-3-(methylamino)butyl]-2-Propenamide
N-[1-methyl-2-(methylamino)propyl]-2-Propenamide.

In particularly preferred embodiments, the free base (IB) is selected from the group consisting of:
2-(Dimethylamino)ethyl acrylate
2-(Diethylamino)ethyl acrylate
2-(Diethylamino)ethyl methacrylate
2-(Dimethylamino)ethyl methacrylate and
2-(tert-Butylamino)ethyl methacrylate.

These free bases can be easily brought to a liquid state and are readily available.

Preferably, the base salt (IA) is a halogen salt of the free base (IB) mentioned above.

Preferably, the cation (I) is a quaternerization of the free base (IB) mentioned above.

Preferred Formulas of Anion (II)—(VI), Acid Salt (IIA)-(VIA), Free Acid (IIB)—(VIB)

Preferably, R6 is H or CH3.
Preferably, R7 is H or CH3.
Preferably, Y is O.
Preferably, R8 is CH2-CH2 or C(CH3)2.
Preferably, Z is SO3.
Preferably, R9 is H or CH3.
Preferably, V is O.
Preferably, W is O.
Preferably, R10 is CH2 or CH2-CH2.
Preferably, n is 1.

Examples of particularly preferred embodiments include the following:
(II), (IIA), (IIB) wherein R6 is H
(II), (IIA), (IIB) wherein R6 is CH3
(III), (IIIA), (IIIB) wherein R7 is H, R8 is CH2-CH2, Z is SO3
(III), (IIIA), (IIIB) wherein R7 is H, R8 is C(CH3)2, Z is SO3
(III), (IIIA), (IIIB) wherein R7 is CH3, R8 is CH2-CH2, Z is SO3
(III), (IIIA), (IIIB) wherein R7 is CH3, R8 is C(CH3)2, Z is SO3
(IV), (IVA), (IVB) wherein R9 is H, V is O, n is 1, W is O, R10 is CH2, Z is SO3
(IV), (IVA), (IVB) wherein R9 is H, V is O, n is 1, W is O, R10 is CH2-CH2, Z is SO3
(IV), (IVA), (IVB) wherein R9 is CH3, V is O, n is 1, W is O, R10 is CH2, Z is SO3
(IV), (IVA), (IVB) wherein R9 is CH3, V is O, n is 1, W is O, R10 is CH2-CH2, Z is SO3
(V), (VA), (VB) wherein R7 is H, Y is O, R8 is CH2-CH2
(V), (VA), (VB) wherein R7 is H, Y is O, R8 is C(CH3)2
(V), (VA), (VB) wherein R7 is CH3, Y is O, R8 is CH2-CH2
(V), (VA), (VB) wherein R7 is CH3, Y is O, R8 is C(CH3)2
(VI), (VIA), (VIB) wherein R9 is H, V is O, n is 1, W is O, R10 is CH2
(VI), (VIA), (VIB) wherein R9 is H, V is O, n is 1, W is O, R10 is CH2-CH2
(VI), (VIA), (VIB) wherein R9 is CH3, V is O, n is 1, W is O, R10 is CH2
(VI), (VIA), (VIB) wherein R9 is CH3, V is O, n is 1, W is O, R10 is CH2-CH2

Preferably, the free acid (IIB), (IIIB), (IVB), (VB) and (VIB) is selected from the group consisting of:
Acrylic acid
Methacrylic acid
2-methyl-2-[(1-oxo-2-propen-1-yl)amino]-1-Propanesulfonic acid
2-methyl-1-[(1-oxo-2-propen-1-yl)amino]-1-Propanesulfonic acid
1-[(1-oxo-2-propen-1-yl)amino]-2-Butanesulfonic acid
2-[(2-methyl-1-oxo-2-propen-1-yl)amino]-2-Propanesulfonic acid
1-[(1-oxo-2-propen-1-yl)amino]-Ethanesulfonic acid
2-(phosphonooxy)ethylester-2-Propenoic acid
2-Propenoic acid, 2-methyl-, 2-(phosphonooxy)ethyl ester
2-methyl-, 1-methyl-3-(phosphonooxy)propyl ester-2-Propenoic acid
2-methyl-, 1-[(phosphonooxy)methyl]propyl ester-2-Propenoic acid,
2-methyl-N-[7-(phosphonooxy)heptyl]-2-Propenamide
4-(phosphonooxy)butyl ester-2-Propenoic acid
2-methyl-, 12-(phosphonooxy)dodecyl ester-2-Propenoic acid
2-methyl-, 10-(phosphonooxy)decyl ester-2-Propenoic acid,
2-methyl-, 6-(phosphonooxy)hexyl ester-2-Propenoic acid
2-methyl-, 3-(phosphonooxy)propyl ester-2-Propenoic acid
2-methyl-, 1-methyl-2-(phosphonooxy)ethyl ester-2-Propenoic acid
3-(phosphonooxy)propyl ester-2-Propenoic acid
2-methyl-, 4-(phosphonooxy)butyl ester-2-Propenoic acid,
2-oxo-2-[[[(1-oxo-2-propen-1-yl)amino]methyl]amino]-Ethanesulfonic acid (CAS #801176-33-0),
2-[[[(2-methyl-1-oxo-2-propen-1-yl)amino]methyl]amino]-2-oxo-Ethanesulfonic acid (CAS #19619-38-6).

Preferably, the acid salt (IIA), (IIIA), (IVA), (VA) and (VIA) is a an alkali metal salt of the free acid mentioned above.

Preferably, the anion (II), (III), (IV), (V) and (VI) is a deprotonated version of the free acid (IIB), (IIIB), (IVB), (VB) and (VIB) mentioned above, respectively.

For the preparation of the ion pair compound according to the invention, the molar ratio between the base salt (IA) or the free base (IB) and the acid salt (IIA), (IIIA), (IVA), (VA) or (VIA) or the free acid (IIB), (IIIB), (IVB), (VB) or (VIB) to be mixed may be 10:1 to 1:10. Preferably, the molar ratio between the base salt (IA) or the free base (IB) and the acid salt (IIA), (IIIA) or (IVA) or the free acid (IIB), (IIIB) or (IVB) to be mixed is 2:1 to 1:2, more preferably 1.5:1 to 1:1.5, more preferably 1.1:1 to 1:1.1. Preferably, the molar ratio between the base salt (IA) or the free base (IB) and the acid salt (VA) or (VIA) or the free acid (VB) or (VIB) to be mixed is 3:1 to 1:1, more preferably 2.5:1 to 1.5:1, more preferably 2.1:1 to 1.9:1.

Most preferably, the molar ratio between the base salt (IA) or the free base (IB) and the acid salt (IIA), (IIIA), (IVA), (VA) or (VIA) or the free acid (IIB), (IIIB), (IVB), (VB) or (VIB) to be mixed is stoichiometric. Thus, most preferably, the molar ratio between the base salt (IA) or the free base (IB) and the acid salt (IIA), (IIIA) or (IVA) or the free acid (IIB), (IIIB) or (IVB) to be mixed is 1:1 and the molar ratio between the base salt (IA) or the free base (IB) and the acid salt (VA) or (VIA) or the free acid (VB) or (VIB) to be mixed is 2:1. The resulting product then does not comprise excess base or acid or excess base salt or acid salt. Advantageously, the resulting product can be directly used without removing excess base or acid or excess base salt or acid salt for the ethylene copolymerization to obtain the ethylene copolymer according to the invention.

If non-stoichiometric ratio is used, the resulting product contains the ion pair compound according to the invention and excess base or acid or excess base salt or acid salt. Preferably, the ion pair compound is isolated from the resulting product before being used for the ethylene copolymerization.

Copolymerization Process

The invention provides a process for producing an ethylene copolymer by copolymerizing ethylene and an ion pair compound consisting of a cation of formula (I) and an acid anion selected from formulas (II), (III), (IV), (V) and (VI).

In some embodiments, ethylene and the ion pair compound are copolymerized in the absence of excess base (IB) or acid (IIB)—(VIB) or excess base salt (IA) or acid salt (IIA)-(VIA). This can be achieved by making the ion pair compound by a process wherein the molar ratio between the base salt or the free base and the acid salt or the free acid to be mixed for making the ion pair compound is stoichiometric and using the resulting product for the copolymerization of ethylene and the ion pair compound. Alternatively, this can be achieved by making the ion pair compound by a process wherein the molar ratio between the base salt or the free base and the acid salt or the free acid to be mixed for making the ion pair compound is non-stoichiometric and isolating the ion pair compound from the resulting product before being used for the ethylene copolymerization.

In some embodiments, ethylene and the ion pair compound are copolymerized in the presence of excess base (IB) or acid (IIB)—(VIB) or excess base salt (IA) or acid salt (IIA)-(VIA). This can be achieved by making the ion pair compound by a process wherein the molar ratio between the base salt or the free base and the acid salt or the free acid to be mixed for making the ion pair compound is non-stoichiometric. If the ion pair compound is not isolated from the resulting product before being used for the ethylene copolymerization, excess base (IB) or acid (IIB)—(VIB) or excess base salt (IA) or acid salt (IIA)-(VIA) is present during the ethylene copolymerization.

Preferably, the process for producing an ethylene copolymer further comprises the process for making the ion pair compound according to the invention, wherein the molar ratio between the base salt (IA) or the free base (IB) and the acid salt (IIA), (IIIA) or (IVA) or the free acid (IIB), (IIIB) or (IVB) to be mixed is 1:1 and the molar ratio between the base salt (IA) or the free base (IB) and the acid salt (VA) or (VIA) or the free acid (VB) or (VIB) to be mixed is 2:1.

The invention further provides the ethylene copolymer obtained by this process.

The ion pair compound according to the invention can be dissolved in various types of common polar organic solvents such as isopropanol, acetonitrile, ethyl acetate and injected in the polymerization reactor as a solution.

The copolymerization may be performed under known processes.

Preferably, the ethylene copolymer according to the invention are produced in a high-pressure free-radical polymerisation process. An advantage of polymerisation in such high-pressure free-radical process is that the polymerisation may be performed without the need for a catalyst being present. This allows for the use of certain comonomers such as polar comonomers which are not suitable as comonomers in the production of ethylene copolymers via catalytic processes such as using Ziegler-Natta type catalysts because of the interference with such catalyst.

A further advantage of preparation of the ethylene copolymer according to the invention in a high-pressure free-radical polymerisation process is that such polymerisation results in ethylene copolymers having a certain degree of long-chain branching. In order to qualify for certain applications, including extrusion coating application, ethylene copolymers are required to have a certain degree of such long-chain branching. The presence of such long-chain branching is understood to contribute to the desired melt processing properties. Accordingly, it is preferred that the ethylene copolymer according to the present invention is prepared via a high-pressure free-radical polymerisation process. The pressure in such high-pressure free-radical polymerisation process preferably is in the range of $\geq 180$ MPa and $\geq 350$ MPa, preferably $\geq 200$ MPa and $\leq 300$ MPa. The temperature in such high-pressure free-radical polymerisation process preferably is in the range of $\geq 100$ and $\leq 350°$ C., preferably $\geq 150$ and $\leq 310°$ C., preferably $\geq 190$ and $\leq 260°$ C., more preferable $\geq 200$ and $\leq 250°$ C.

Such high-pressure free-radical polymerisation process may for example be performed in a tubular reactor. Such tubular reactor may for example be a reactor such as described in Nexant PERP Report 2013-2, 'Low Density Polyethylene', pages 31-48.

Such tubular reactor may for example be operated at pressures ranging from 150 to 300 MPa. The tubular reactor may have a tube length of for example $\geq 1000$ m and $\leq 5000$ m. The tubular reactor may for example have a ratio of length to inner diameter of $\geq 1000:1$, alternatively $\geq 10000:1$, alternatively $\geq 25000:1$, such as $\geq 10000:1$ and $\leq 50000:1$, alternatively $\geq 25000:1$ and $\leq 35000:1$. The residence time in the tubular reactor may for example be $\geq 30$ s and $\leq 300$ s, alternatively $\geq 60$ s and $\leq 200$ s. Such tubular reactors may for example have an inner tubular diameter of $\geq 0.01$ m and $\leq 0.20$ m, alternatively $\geq 0.05$ m and $\leq 0.15$ m. The tubular reactor may for example have one or more inlet(s) and one or more outlet(s). The feed composition may for example be fed to the tubular reactor at the inlet of the tubular reactor. The stream that exits the tubular reactor from the outlet may for example comprise the ethylene copolymer. The stream that exits the tubular reactor from the outlet may for example comprise unreacted feed composition. Such unreacted feed compositions may be recycled back into the tubular reactor via one or more inlet.

The high-pressure free-radical polymerisation process is performed in the presence of one or more free-radical initiator. Preferably, the free-radical initiator is selected from organic peroxides and/or azo compounds.

Suitable organic peroxides may for example include diacyl peroxides, dialkyl peroxides, peroxymonocarbonates, peroxydicarbonates, peroxyketals, peroxyesters, cyclic peroxides, hydroperoxides. Suitable azo compounds may for example include 2,2'-azodi(isobutyronitrile), 2,2'-azodi(2-methylbutyronitrile), 1,1'-azodi(hexahydrobenzonitrile).

Examples of suitable diacyl peroxides are diisobutyryl peroxide, di(3,5,5-trimethylhexanoyl) peroxide, dilauroyl peroxide, didecanoyl peroxide, dibenzoyl peroxide.

Examples of suitable dialkyl peroxides are dicumyl peroxide, di(tert-butylperoxyisopropyl)benzene, 2,5-dimethyl-2,5-di(tert-butylperoxy)hexane, tert-butyl cumyl peroxide, 2,5-dimethyl-2,5-di(tert-butylperoxy)hexyne, di-tert-butyl peroxide, di-isononanoyl peroxide, di-tert-amyl peroxide, didecanoyl peroxide.

Examples of suitable peroxymonocarbonates are tert-amylperoxy 2-ethylhexyl carbonate, tert-butylperoxy isopropyl carbonate, tert-butylperoxy 2-ethylhexyl carbonate.

Examples of suitable peroxydicarbonates are di(3-methoxybutyl)peroxydicarbonate, di-sec-butyl peroxydicarbonate, diisopropyl peroxydicarbonate, di(4-tert-butylcyclohexyl) peroxydicarbonate, di(2-ethylhexyl) peroxydicarbonate, dibutyl peroxydicarbonate, diacetyl peroxy dicarbonate, dimyristyl peroxydicarbonate, dicyclohexyl peroxydicarbonate.

Examples of suitable peroxyketals are 1,1-di(tert-butyl peroxy)-3,5,5-trimethylcyclohexane, 1,1-di(tert-amyl peroxy)cyclohexane, 1,1-di(tert-butyl peroxy)cyclohexane, 2,2-di(tert-butyl peroxy)butane, butyl 4,4-di(tert-butyl peroxy)valerate, n-ethyl-4,4-di-(tert-butylperoxy)valerate, ethyl-3,3-di(tert-butylperoxy)butyrate, ethyl-3,3-di(tert-amylperoxy)butyrate.

Examples of suitable peroxyesters are cumyl peroxyneodecanoate, 1,1,3,3,-tetramethylbutylperoxyneodecanoate, cumyl peroxyneoheptanoate, tert-amyl peroxyneodecanoate, tert-butyl peroxyneodecanoate, tert-butyl peroxyisononanoate, tert-butyl permaleate, tert-butyl peroxydiethylisobutyrate, 1,1,3,3-tetramethylbutyl peroxypivalate, tert-butyl peroxyneoheptanoate, tert-amyl peroxypivalate, tert-butyl peroxypivalate, 2,5-dimethyl-2,5-di(2-ethylhexanoylperoxy)hexane, 1,1,3,3-tetramethylbutyl peroxy-2-ethylhexanoate, tert-amyl peroxy-2-ethylhexanoate, tert-butyl peroxy-2-ethylhexanoate, tert-butyl peroxydiethylacetate, tert-butyl peroxyisobutyrate, tert-amyl peroxyacetate, tert-butyl peroxy-3,5,5-trimethylhexanoate, tert-amyl peroxybenzoate, tert-butyl peroxyacetate, tert-butyl peroxybenzoate. Examples of suitable cyclic peroxides are 3,6,9-triethyl-3,6,9-trimethyl-1,4,7-triperoxononane, 3,3,5,7,7-pentamethyl-1,2,4-trioxepane, 3,3,6,6,9,9,-hexamethyl-1,2,4,5-tetraoxacyclononane.

Examples of suitable hydroperoxides are isopropylcumyl hydroperoxide, 1,1,3,3-tetramethylbutyl hydroperoxide, cumyl hydroperoxide, tert-butyl hydroperoxide, tert-amyl hydroperoxide, methyl isobutyl ketone hydroperoxide, diisopropyl hydroxyperoxide.

Preferably the free radical initiator composition is selected from 2,5-dimethyl-2,5-di(tert-butylperoxy)hexane, t-butyl peroxy pivalate (t-BPP) and/or t-butyl peroxy benzoate (t-BPB).

Such initiators may for example be fed to the tubular reactor in a pure form or as a solution in a solvent. As solvent, for example a $C_2$-$C_{20}$ normal paraffin or $C_2$-$C_{20}$ isoparaffin may be used. For example, such solution may comprise ≥2.0% and ≤65.0% by weight of initiator, alternatively ≥5.0% and ≤40.0% by weight, alternatively ≥10.0% and ≤30.0% by weight, compared to the total weight of the solution.

Such initiators may for example be introduced into the polymerisation reactor in quantities of ≤300 ppm, preferably ≤200 ppm, compared to the total weight of the materials fed to the polymerisation reactor.

In addition, further modifiers may be fed to the tubular reactor. Examples of such modifiers may include inhibitors, scavengers and/or chain transfer agents, such as alcohols, aldehydes, ketones and aliphatic hydrocarbons. Such modifiers may for example be fed to the tubular reactor in a pure form or as a solution in a solvent. Examples of suitable chain transfer agents include cyclopropane, methane, t-butanol, perfluoropropane, deuterobenzene, ethane, ethylene oxide, 2,2-dimethylpropane, benzene, dimethyl sulfoxide, vinyl methyl ether, methanol, propane, 2-methyl-3-buten-2-ol, methyl acetate, t-butyl acetate, methyl formate, ethyl acetate, butane, triphenylphosphine, methylamine, methyl benzoate, ethyl benzoate, N,N-diisopropylacetamide, 2,2,4-trimethylpentane, n-hexane, isobutane, dimethoxymethane, ethanol, n-heptane, n-butyl acetate, cyclohexane, methylcyclohexane, 1,2-dichlorethane, acetronitrile, N-ethylacetamide, propylene, n-decane, N,N-diethylacetamide, cyclopentane, acetic anhydride, n-tridecane, n-butyl benzoate, isopropanol, toluene, acetone, 4,4-dimethylpentene-1, trimethylamine, N,N-dimethylacetamide, isobutylene, n-butyl isocyanate, methyl butyrate, n-butylamine, N,N-dimethylformamide, diethyl sulfide, diisobutylene, tetrahydrofuran, 4-methylpentene-1, p-xylene, p-dioxane, trimethylamine, butene-2, 1-bromo-2-chlorethane, octene-1,2-methylbutene-2, cumene, butene-1, methyl vinyl sulfide, n-butyronitrile, 2-methylbutene-1, ethylbenzene, n-hexadecene, 2-butanone, n-butyl isothiocyanate, methyl 3-cyanopropionate, tri-n-butylamine, 3-methyl-2-butanone, isobutyronitrile, di-n-butylamine, methyl chloroacetate, 3-methylbutene-1, 1,2-dibromoethane, dimethylamine, benzaldehyde, chloroform, 2-ethylhexene-1, propionaldehyde, 1,4-dichlorobutene-2, tri-n-butylphosphine, dimethylphosphine, methyl cyanoacetate, carbon tetrachloride, bromotrichloromethane, di-n-butylphosphine, acetaldehyde, hydrogen and phosphine.

Preferably, the polymerization is performed in the presence of a chain transfer agent selected from the group consisting of methanol, propionaldehyde, n-heptane, propane, isopropanol and acetone.

The quantity of the chain transfer agent is preferably in the range between 0.01 and 2 mole %, compared to the total weight of the materials fed to the polymerisation reactor.

No neutralization step is required after the copolymerization step.

Ethylene Copolymer

The ethylene copolymer obtained according to the process of the invention was found to have a high dielectric constant. The dielectric constant is surprisingly high especially in relation to the amount of the unit derived from the charged compound in the copolymer. The copolymer according to the invention was found to have a resistivity increasing with temperature (positive temperature coefficient). This allows the copolymer according to the invention to be used for applications where high resistivity is required at high temperatures.

Preferably, the amount of the units derived from the ion pair compound in the ethylene copolymer is 0.01 to 10.00 mol %, preferably 0.02 to 5.00 mol %, 0.03 to 1.50 mol %, 0.05 to 1.00 mol %, preferably 0.15 to 1.00 mol %, with respect to the ethylene copolymer.

Preferably, the amount of the units derived from the ion pair compound in the ethylene copolymer is 0.15 to 1.00 mol %. In this case, the copolymer advantageously has a low dependency to the frequency over a wide range of frequencies, i.e. the high dielectric constant observed at relatively low frequencies is also observed at relatively high frequencies.

In preferred embodiments, the ethylene copolymer according to the invention has a dielectric constant of at least 2.50 at 1 Hz and at least 2.50 at $10^5$ Hz measured at 85° C. Preferably, the ethylene copolymer according to the invention further has a dielectric constant of at least 2.50 at 10 Hz, at least 2.50 at $10^2$ Hz, at least 2.50 at $10^3$ Hz and/or at least 2.50 at $10^4$ Hz, measured at 85° C. The measurement of the dielectric constant may be performed by alpha-A dielectric analyzer of the company Novocontrol under the following conditions:

Sample diameter: 40 mm; each face has gold contacts using a sputtering technique (first sputtering; cut out of test sample)

Sample is placed between two gold plated round electrodes; sample cell in placed in temperature chamber under Nitrogen condition.

Electrode thickness: 2 mm
Sample thickness: ~1.5 mm
Ac voltage: auto range (max 3 Volt)
Reference measurements: always; maximum 3 capacitors
Edge compensation: on The invention further relates to a product obtained by heating the ethylene copolymer according to the invention to a temperature of 140 to 220° C. for a period of 1 to 60 minutes (referred herein as a heated product).

Applications

The invention further relates to a composition comprising the ethylene copolymer according to the invention or the heated product according to the invention. The composition may further comprise additives, e.g. at an amount of 0.01 to 5.0 wt % with respect to the composition.

The invention further relates to an article comprising the ethylene copolymer according to the invention, the heated product according to the invention or the composition according to the invention. The article may be an extrusion coated article, a film, a foam, an adhesive, a bitumen modifier, a moulded article, a 3D printed article or a polymer alloy.

The invention further relates to the use of the ethylene copolymer according to the invention, the heated product according to the invention or the composition according to the invention in the production of extrusion coated articles, films, foams, adhesives, bitumen modifiers, moulded articles, 3D printed articles and/or polymer alloys.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

The invention is now elucidated by way of the following examples, without however being limited thereto.

The ion pair compound (X) was prepared according to method 1.

Method 1: Preparation from Acid Salt and Base Salt

In a round bottom flask, 2-aminoethyl methacrylate hydrochloride (66.3 g, 0.40 mol) was dissolved in 80 mL of methanol and 80 mL of dichloromethane was added. A solution of sodium methacrylate (43.2 g, 0.40 mol) in 300 mL methanol was added which led the solution to get turbid. Further addition of dichloromethane (150 mL) led to the full precipitation of sodium chloride which was filtered off. After evaporation of the filtrate, the desired ion pair compound (X) was recovered (86.1 g, 100%). Improved purity was obtained by recrystallization in ethyl acetate (>95% purity, 58% yield).

The ion pair compound (XI) was prepared according to method 2.

Method 2: Preparation from Free Acid and Free Base

In a round bottom flask containing methacrylic acid (510.9 g, 5.935 mol) equipped with an ice bath was added dropwise 2-(Dimethylamino)ethyl methacrylate (1000 mL, 5.935 mol) so that temperature will never exceed 20° C. No purification was needed and the ion pair compound (XI) was obtained in quantitative yield (1.44 kg, 100%).

Copolymerisation of Ethylene with Ion Pair Compound (X) or (XI)

A continuous stirred autoclave reactor was used to produce the material at produces an average of 0.6 kg-LDPE/h, operating at 180 to 220° C., pressure of 2000 barg, and ethylene flow rate of 4 kg/h with a single monomer and peroxide injection. Total volume is 110 ml, effective volume is 99 ml.

The copolymerization of ethylene and the ion pair compound X is represented as follows (a, b and c fragments are randomly distributed):

Raw Materials Used
  Ethylene: purity >99.9%—Oxygen <5 ppm
  ion pair comonomer X or XI: purity >90%
  Isopropanol: purity >99%
Polymerization Parameters:
  Pressure 2000 bars
  Ethylene flow rate was fixed at around 4 kg/h (residence time ~50 s)
  The impeller velocity was fixed at 1540 rpm
  Peroxide: Luperox 11M75
  Temperature of polymerization: 200° C.
  comonomer flow: 0.2 mol % ion pair compound X or XI in the ethylene feed (as a solution in isopropanol)

The amount of the ion pair compound was varied as shown in Table 1. Table 1 shows the comonomer content and the cationic charge per 1000 C of the obtained copolymers as well as those of Surlyn 8920.

TABLE 1

| Name | Ion Pair Compound (comonomer) | Reactor Feed (mol %) | Comonomer content (mol %) | Comonomer content (wt %) | Cationic charge/ 1000 C |
|---|---|---|---|---|---|
| Ex 1 | X | 0.05 | 0.09 | 0.64 | 0.44 |
| Ex 2 | X | 0.1 | 0.32 | 2.35 | 1.5 |
| Ex 3 | XI | 0.05 | 0.15 | 1.3 | 0.75 |
| Ex 4 | XI | 0.1 | 0.25 | 2.17 | 1.27 |
| Surlyn 8920 | | | 5.4 | 14.5 | 28 |

DSC

Melting temperatures (Tm) and enthalpies of the transition (ΔHm) were measured by differential scanning calorimetry (DSC) using a DSC Q100 from TA Instruments. The measurements were carried out at a heating and cooling rate of 10° C./min from −20° C. to 150° C. The transitions were deduced from the second heating. The DSC results show that the ethylene copolymers of Ex 1, 2, 3 and 4 are semi-crystalline and have a low enough Tm that allows easy processability.

Dielectric Constant

The resistivity and dielectric constant were measured for the ethylene copolymers of Ex 1, 2, 3, 4, Surlyn 8920 and LDPE 2100 (SABIC) at 23° C., 50° C. and 85° C. The measurement of the dielectric constant was performed by alpha-A dielectric analyzer of the company Novocontrol under the following conditions:

Sample diameter: 40 mm; each face has gold contacts using a sputtering technique (first sputtering; cut out of test sample)
  Sample is placed between two gold plated round electrodes; sample cell in placed in temperature chamber under Nitrogen condition.
  Electrode thickness: 2 mm
  Sample thickness: ~1.5 mm
  Ac voltage: auto range (max 3 Volt)
  Reference measurements: always; maximum 3 capacitors
  Edge compensation: on

Figure 1:
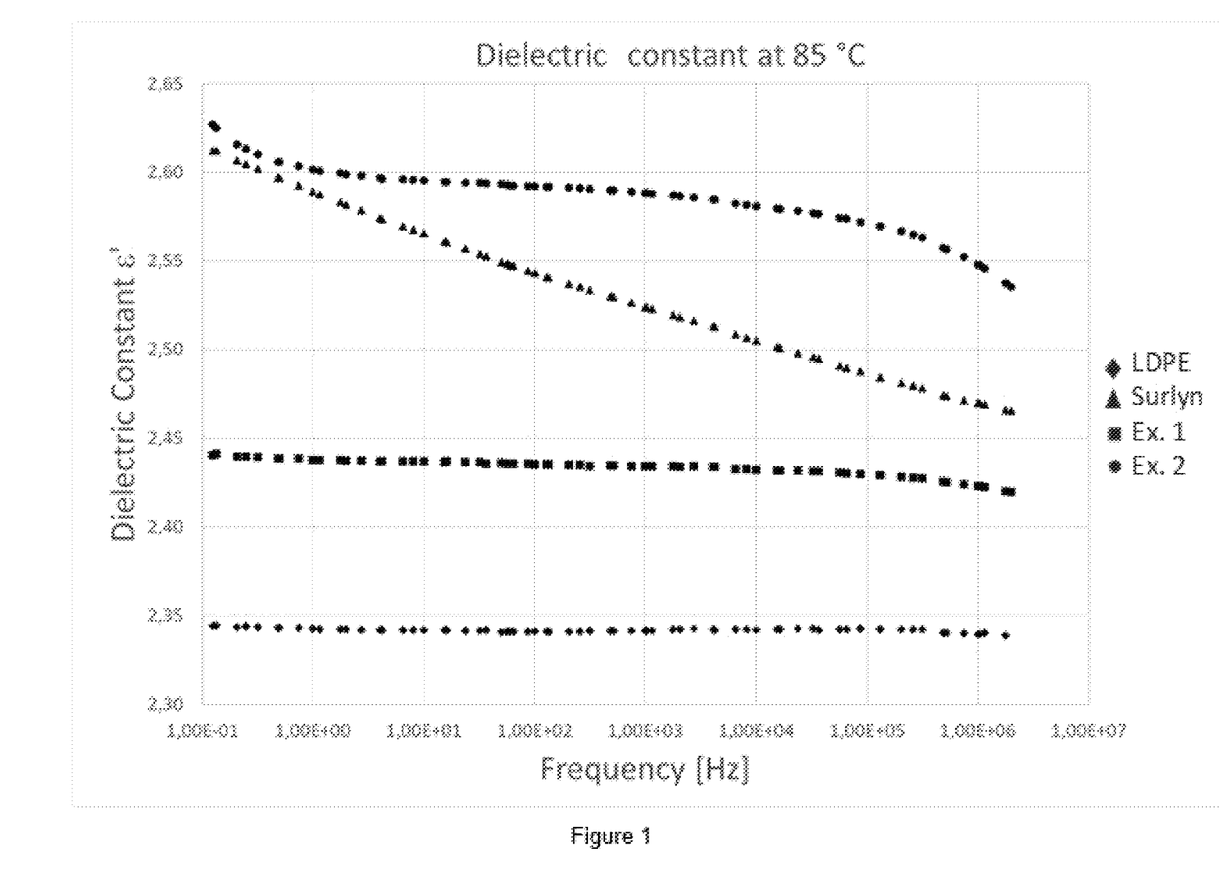
FIG. 1 is a graph of Dielectric Constant versus Frequency.

The results are shown in FIG. 1. Compared to Surlyn 8920, the copolymer of Ex 2 has a higher dielectric constant although the amount of the charged unit in the copolymer is substantially lower.

The dielectric constants of the copolymers of Ex 1 and 2 have a low dependency on the frequency over a wide range of frequencies, compared to Surlyn 8920.

Figure 2:
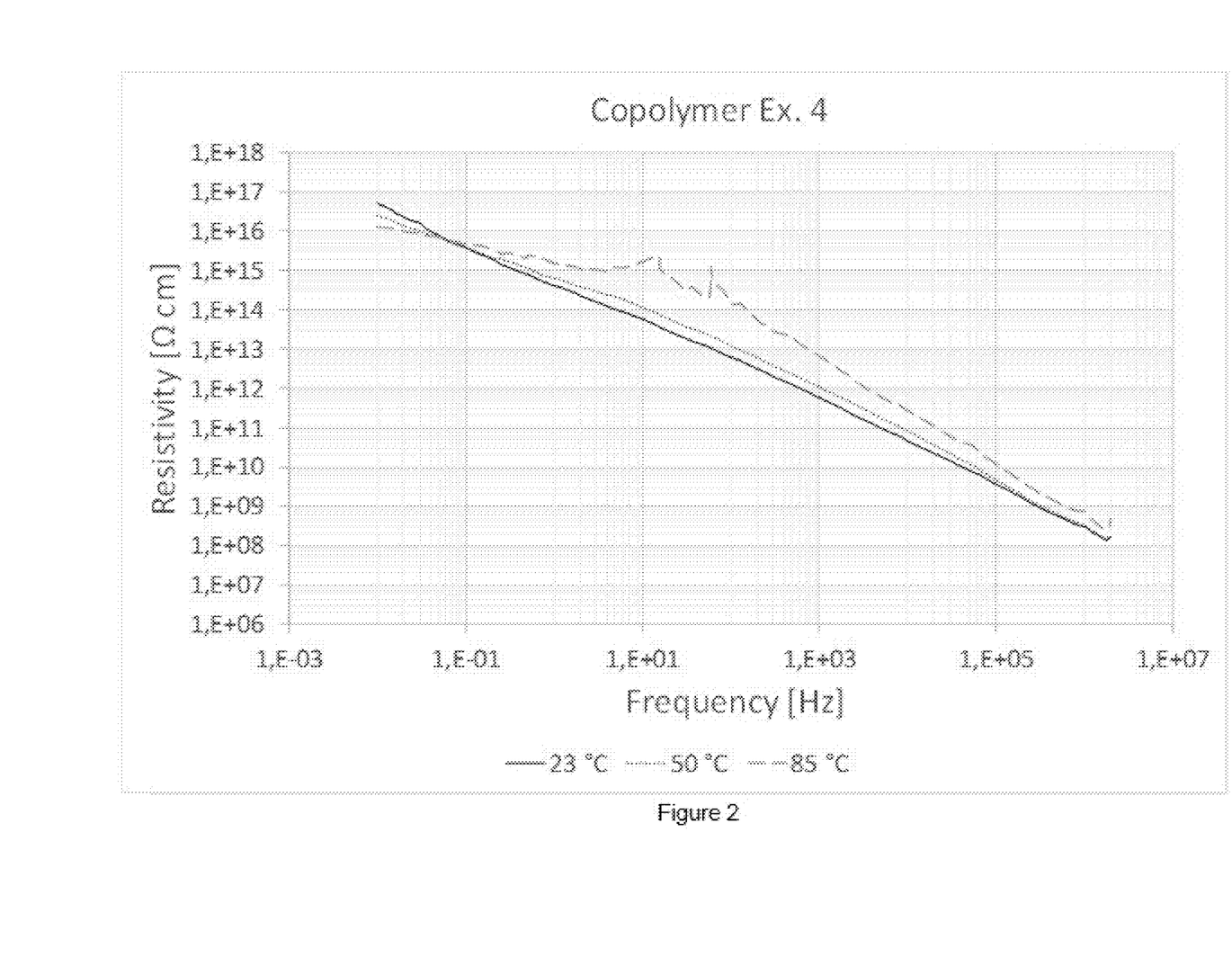
FIG. 2 is a graph of Resistivity versus Frequency.

Similarly, the resistivity was measured for the ethylene copolymer of Ex 4 at varying temperatures. The results are shown in FIG. 2. The resistivity of the ethylene copolymer of Ex 4 increases with increasing temperature.

The invention claimed is:

1. An ethylene copolymer obtained by copolymerizing ethylene and an ion pair compound consisting of a cation of formula (I) and an anion selected from formulas (II), (III), (IV) and (V), wherein in formula (I), $R_1$ is H or C1-C10 alkyl; X is O or NH; $R_2$ is C1-C40 alkyl; each of $R_3$ and $R_4$ is independently H or C1-C10 alkyl, or $R_3$ and $R_4$ are connected through a cyclic structure, and $R_5$ is H or C1-C20, wherein in formulas (II) to (V), each of $R_6$, $R_7$, and $R_9$ is independently H or C1-C10 alkyl; each of $R_8$ and $R_{10}$ is independently C1-C40 alkyl; each of Y, V, and W is independently O or NH;
n is 1 to 20; and Z is —SO$_3$ or —C(O)O,
with the proviso that the ion pair compound does not comprise , or 2-methacryloyloxyethyltrimethylammonium and 2-acrylamido-2-methylpropane sulfonate, or 2-methacryloyloxyethyltrimethylammonium and 2-methacryloyloxyethane sulfonate.

2. The ethylene copolymer according to claim 1, wherein $R_5$ is H.

3. The ethylene copolymer according to claim 1, wherein $R_1$=H or CH3; X=O; $R_2$=CH2-CH2; and/or $R_3$=$R_4$=$R_5$=H; $R_3$=$R_4$=CH3, $R_5$=H; $R_3$=$R_4$=CH2CH3, $R_5$=H; $R_3$=tButyl, $R_4$=$R_5$=H or $R_3$=$R_4$=$R_5$=CH3.

4. The ethylene copolymer according to claim 1, wherein the cation (I) is a quaternerization of a free base (IB) selected from the group consisting of:
2-(dimethylamino)ethyl acrylate,
2-(diethylamino)ethyl acrylate,
2-(diethylamino)ethyl methacrylate,
2-(dimethylamino)ethyl methacrylate,
2-(tert-butylamino)ethyl methacrylate,
N-[3-(hexahydro-1H-azepin-1-yl)-1,1-dimethylpropyl]-2-propenamide,
N-[2-(tetrahydro-1,4-oxazepin-4(5H)-yl)ethyl]-2-propenamide,
N-[2-[methyl(tetrahydro-2H-pyran-4-yl)amino]ethyl]-2-propenamide,
N-[3-(hexahydro-4-methyl-1H-1,4-diazepin-1-yl)propyl]-2-propenamide,
N-[1-methyl-2-(methylamino)propyl]-2-propenamide,
N-[2-(methylamino)propyl]-2-propenamide,
N-[2-methyl-2-(methylamino)propyl]-2-propenamide,
N-[1-methyl-2-(methylamino)ethyl]-2-propenamide,
N-[1-methyl-3-(methylamino)butyl]-2-propenamide, and
N-[1-methyl-2-(methylamino)propyl]-2-propenamide.

5. The ethylene copolymer according to claim 1, wherein the anion (II), (III), (IV), or (V) is a deprotonated version of a free acid (IIB), (IIIB), (IVB), or (VB) selected from the group consisting of:
acrylic acid,
methacrylic acid,
2-methyl-2-[(1-oxo-2-propen-1-yl)amino]-1-propanesulfonic acid,
2-methyl-1-[(1-oxo-2-propen-1-yl)amino]-1-propanesulfonic acid,
1-[(1-oxo-2-propen-1-yl)amino]-2-butanesulfonic acid,
2-[(2-methyl-1-oxo-2-propen-1-yl)amino]-2-propanesulfonic acid,
1-[(1-oxo-2-propen-1-yl)amino]-ethanesulfonic acid,
2-(phosphonooxy)ethylester-2-propenoic acid,
2-propenoic acid, 2-methyl-, 2-(phosphonooxy)ethyl ester,
2-methyl-, 1-methyl-3-(phosphonooxy)propyl ester-2-propenoic acid,
2-methyl-, 1-[(phosphonooxy)methyl]propyl ester-2-propenoic acid,
2-methyl-N-[7-(phosphonooxy)heptyl]-2-propenamide,
4-(phosphonooxy)butyl ester-2-propenoic acid,
2-methyl-, 12-(phosphonooxy)dodecyl ester-2-propenoic acid,
2-methyl-, 10-(phosphonooxy)decyl ester-2-propenoic acid,
2-methyl-, 6-(phosphonooxy)hexyl ester-2-propenoic acid,
2-methyl-, 3-(phosphonooxy)propyl ester-2-propenoic acid,
2-methyl-, 1-methyl-2-(phosphonooxy)ethyl ester-2-propenoic acid,
3-(phosphonooxy)propyl ester-2-propenoic acid,
2-methyl-, 4-(phosphonooxy)butyl ester-2-propenoic acid,
2-oxo-2-[[[(1-oxo-2-propen-1-yl)amino]methyl]amino]-ethanesulfonic acid, and
2-[[[(2-methyl-1-oxo-2-propen-1-yl)amino]methyl]amino]-2-oxo-ethanesulfonic acid.

6. The ethylene copolymer according to claim 1, wherein an amount of units derived from the ion pair compound in the ethylene copolymer is 0.01 to 10.00 mol %.

7. The ethylene copolymer according to claim 1, wherein the ethylene copolymer has a dielectric constant of at least 2.50 at 1 Hz and at least 2.50 at $10^5$ Hz measured at 85° C.

8. A product obtained by heating the ethylene copolymer according to claim 1 at a temperature of 140 to 220° C. for a period of 1 to 60 minutes.

9. An article comprising the ethylene copolymer according to claim 1.

10. A process for producing the ethylene copolymer according to claim 1 by copolymerizing ethylene and the ion pair compound.

11. The process according to claim 10, wherein ethylene and the ion pair compound are copolymerized in the absence of excess base or acid or excess base salt or acid salt for making the ion pair compound.

12. The process according to claim 10, wherein the process for producing the ethylene copolymer further comprises a process for making the ion pair compound, wherein a molar ratio between the base salt or the free base and the acid salt or the free acid to be mixed for making the ion pair compound is stoichiometric.

13. The process according to claim 10, wherein ethylene and the ion pair compound are copolymerized in the presence of excess base or acid or excess base salt of acid salt for making the ion pair compound.

14. The process according to claim 10, wherein the process for producing the ethylene copolymer further comprises a process for making the ion pair compound, wherein a molar ratio between the base salt or the free base and the acid salt or the free acid to be mixed for making the ion pair compound is non-stoichiometric.

15. The ethylene copolymer according to claim 1, wherein $R_6$ is H or CH3; $R_7$ is H or CH3; Y is O; $R_8$ is CH2-CH2 or C(CH3)2; Z is SO3; $R_9$ is H or CH3; V is O; W is O; and $R_{10}$ is CH2 or CH2-CH2.

16. The ethylene copolymer according to claim 15, wherein n is 1.

17. The ethylene copolymer according to claim 3, wherein $R_6$ is H or CH3; $R_7$ is H or CH3; Y is O; $R_8$ is CH2-CH2 or C(CH3)2; Z is SO3; $R_9$ is H or CH3; V is O; W is O; and $R_{10}$ is CH2 or CH2-CH2.

18. The ethylene copolymer according to claim 17, wherein n is 1.

* * * * *